United States Patent [19]

Ushikubo

[11] Patent Number: 5,424,036

[45] Date of Patent: Jun. 13, 1995

[54] AUTOMATIC ANALYZER

[75] Inventor: Masao Ushikubo, Hachioji, Japan

[73] Assignee: Olympus Optical Co., Ltd., Tokyo, Japan

[21] Appl. No.: 52,469

[22] Filed: Apr. 26, 1993

[30] Foreign Application Priority Data

Apr. 24, 1992 [JP] Japan .................................. 4-106742

[51] Int. Cl.⁶ .......................................... G01N 35/00
[52] U.S. Cl. ........................................ 422/64; 422/63;
422/100; 422/102; 422/104; 436/43; 436/47; 436/50
[58] Field of Search ...................... 422/63, 64, 67, 99, 422/102, 104, 100; 436/43, 47, 50

[56] References Cited

U.S. PATENT DOCUMENTS

| | | | |
|---|---|---|---|
| 4,287,155 | 9/1981 | Tersteeg et al. | 422/64 |
| 4,313,735 | 2/1982 | Yamashita et al. | 23/230 R |
| 4,346,056 | 8/1982 | Sakurada | 422/64 |
| 4,455,280 | 7/1984 | Shinohara et al. | 422/63 |
| 4,456,581 | 6/1984 | Edelmann et al. | 422/72 |
| 4,699,767 | 10/1987 | Aihara | 422/65 |
| 4,751,186 | 6/1988 | Baisch et al. | 436/47 |
| 4,764,342 | 8/1988 | Kelln et al. | 422/72 |
| 4,814,144 | 3/1989 | Edelmann et al. | 422/102 |
| 4,849,176 | 7/1989 | Sakagami | 422/64 |
| 4,849,177 | 7/1989 | Jordan | 422/64 |
| 4,900,513 | 2/1990 | Barker et al. | 422/64 |
| 4,919,887 | 4/1990 | Wakatake | 422/67 |
| 4,961,906 | 10/1990 | Andersen et al. | 422/102 |
| 4,970,053 | 11/1990 | Fechtner | 422/102 |
| 5,051,238 | 9/1991 | Umetsu et al. | 422/64 |
| 5,149,501 | 9/1992 | Babson et al. | 422/58 |
| 5,167,922 | 12/1992 | Long | 422/58 |

FOREIGN PATENT DOCUMENTS

| | | |
|---|---|---|
| 0289789 | 11/1988 | European Pat. Off. . |
| 0325101 | 7/1989 | European Pat. Off. . |
| 0355823 | 2/1990 | European Pat. Off. . |
| 0445616 | 9/1991 | European Pat. Off. . |
| 3031430 | 3/1981 | Germany . |
| 3044372 | 7/1982 | Germany . |
| 3405292 | 9/1985 | Germany . |
| 3717907 | 12/1987 | Germany . |
| 3839080 | 6/1989 | Germany . |
| 3306491 | 12/1989 | Germany . |

*Primary Examiner*—James C. Housel
*Assistant Examiner*—Long V. Le
*Attorney, Agent, or Firm*—Stevens, Davis, Miller & Mosher

[57] ABSTRACT

An automatic analyzer including a sampler for delivering given amounts of samples into reaction vessels arranged along a reaction line, a reagent tray for holding a plurality of reagents, a reagent delivery device for delivering given amounts of reagents into the reaction vessels, and a measuring device for measuring test liquids in the reaction vessels, the reagent tray includes a turn table, a plurality of divided trays detachably provided on the turn table and having a plurality of compartments, and a plurality of reagent containers containing the reagents and being installed into compartments of divided trays. An identification code is provided on respective divided trays for identifying the division information, and a reagent identifying label is provided on a respective reagent container for identifying a respective reagent. The reagent delivery device includes a first detector for detecting said identification code on the divided tray and a second detector for detecting said reagent identification label. In this manner any desired reagent container can be indexed into a reagent sucking position in accordance with the division information, reagent information and a test item to be analyzed. The number and size of the compartments in the divided tray are set such that a plurality of reagent containers having different sizes can be effectively set on the divided tray, and thus a large number of reagent containers having different volumes may be efficiently arranged on the reagent table to perform rapid and adequate analysis and make unnecessary frequent exchange of reagent containers.

18 Claims, 6 Drawing Sheets

FIG_1

FIG_2

FIG_5A
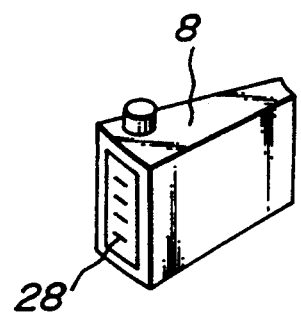
FIG_5B
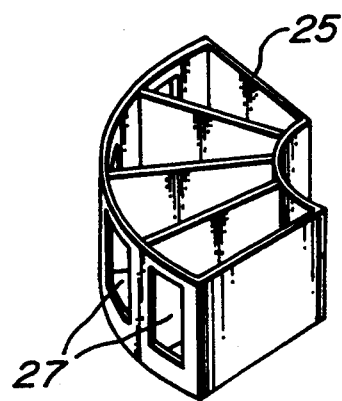

AUTOMATIC ANALYZER

BACKGROUND OF THE INVENTION

1. Field of the Invention

The present invention relates to an automatic analyzer in which a sample such as serum, urine or the like taken out of a patient and a reagent necessary to analyze a given component contained in this sample are dispensed into a reaction vessel such as a cuvette or test tube to prepare a test liquid, and this test liquid is measured after a predetermined reaction time period to perform quantitative analysis of the given component contained in the sample.

2. Description of the Related Art

Usually the above mentioned automatic analyzer is constructed to perform the analyses of a plurality of different components. Such an apparatus is generally called a multi-item analyzer. In the multi-item analyzer, a plurality of different kinds of reagents necessary for different analyses are contained in different reagent containers having the same shape and size and these reagent containers are arranged on a turn table at a predetermined equal interval in order to index any desired reagent containers into a reagent sucking position. Amounts of the reagents dispensed from the reagent containers into reaction vessels differ from each other depending on analytic items and analyzing conditions, and spread over a wide range of 25 $\mu$l to 400 $\mu$l.

In addition, there is such a case in which in the reagent containers on the turn table, concentrated reagents which are used after dilution with diluting liquids during dispensing and non-concentrated reagents which are called general reagents are present in a mixed manner. Incidentally, under the same analyzing condition, a volume of 10 ml to 20 ml is allowable in the case of the concentrated reagent, while a volume of 50 ml to 100 ml is necessary in the case of the general reagent.

As described above, when the analytic items and the analyzing conditions are different, or when the concentrated reagents and the general reagents are present on the turn table in a mixed manner, the user sometimes suffers a lack of a necessary reagent on the turn table and occurrence of necessity to frequently exchange reagent containers depending on analytic items. When a lack of a reagent occurs, the analyzing operation must be interrupted. This apparently decreases the efficiency of the analyzer.

In addition, the reagent containers having the same shape and size are arranged on the reagent table at the predetermined interval. That is to say, a reagent container containing a reagent for an item which requires a smaller amount of a reagent occupies the same space on the reagent table as that occupied by another reagent container containing a reagent for a test item using a larger amount of reagent. This causes a problem from a viewpoint of the space utilizing efficiency.

In known multi-item analyzers, a size of the reagent containers is usually determined such that it can contain a sufficient amount of a reagent a large amount of which is consumed, so that the number of reagent containers which can be set on the reagent table is limited and thus the number of items to be performed is also limited.

SUMMARY OF THE INVENTION

The present invention has for its object to provide a novel and useful automatic analyzer, in which the above-mentioned inconvenience of the prior art automatic analyzer can be dissolved and a large number of reagent containers having different volumes can be efficiently arranged on a reagent table, so as to make it possible to perform large kinds of analyses in an efficient manner.

In order to achieve the above-mentioned object, according to the present invention, an automatic analyzer comprises a sample holding means for holing a number of samples to be analyzed and indexing successive samples into a sample sucking position;

a sample dispensing means for dispensing samples indexed into said sample sucking position into reaction vessels;

a reagent holding means for holding a plurality of different kinds of reagents and indexing any desired reagents into a reagent sucking position, said reagent holding means including a turn table, a driving means for rotating said turn table, a plurality of divided trays detachably arranged on said turn table, each divided tray having a plurality of compartments into which reagent containers are detachably installed, a first detector for detecting a position of said turn table to derive a position signal, a second detector for detecting division identification marks provided on said divided trays to provide a division information signal, and a third detector for detecting reagent identification marks provided on respective reagent containers to provide a reagent identification signal;

a reagent dispensing means for dispensing reagents indexed at said reagent sucking position into the reaction vessels;

a measuring means for measuring test liquids contained in the reaction vessels after elapsing given reaction time; and a controlling means for controlling said driving means in the reagent holding means and reagent dispensing means in accordance with said position signal generated by said first detector as well as said division information signal and reagent identification signal generated by said second and third detectors, respectively.

In the automatic analyzer according to the invention, the reagent containers having different volumes can be efficiently arranged on the divided trays, and therefore the rapid and adequate analyzing operation can be performed efficiently while the divided trays on the turn table and the reagent containers installed in the compartments of the divided trays are identified on the basis of the position signal generated by the first detector.

BRIEF DESCRIPTION OF THE DRAWINGS

FIGS. 5A and 5B are perspective views illustrating a set of the divided tray and reagent container;

DESCRIPTION OF THE PREFERRED EMBODIMENTS

Figure 1:
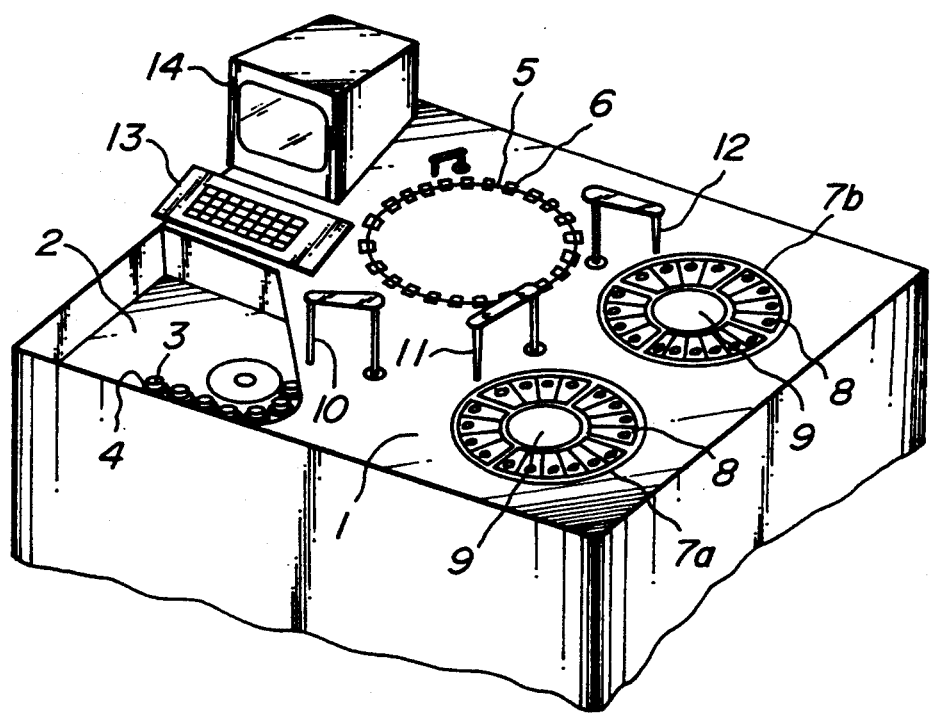
FIG. 1 is a schematic view illustrating an embodiment of the automatic analyzer according to the present invention.

Examples of the present invention will be explained hereinafter with reference to the drawings. FIG. 1 shows schematically an embodiment of the automatic analyzer according to the present invention. On a main body 1 there is arranged a sampler 2 which feeds successive samples into a given sample sucking position intermittently at a certain cycle. To this end, the sampler 2 comprises a plurality of sample cups 3 each accommodating a sample such as serum, urine and the like taken out of patients. The sample cups 3 are held by a holder chain 4 which is moved pitch by pitch to perform the intermittent movement of the sample cups 3.

In addition, on the apparatus main body 1 is arranged a reaction disk 5, which is intermittently rotated in synchronism with the intermittent movement of the holder chain 4 for moving the sample cups 3 of the sampler 2. This reaction disk 5 holds a plurality of cuvettes 6 equidistantly along its circumference.

Further, first and second reagent trays 7a and 7b are arranged on the apparatus main body 1 side by side. In the reagent trays 7a and 7b, a plurality of reagent containers 8 for accommodating reagents necessary for effecting predetermined analytic items are detachably arranged. As will be explained later, according to the invention detectors for identifying the reagent containers 8 are provided in the vicinity of the reagent trays. Further, the reagent trays 7a and 7b are installed on respective turn tables as described hereinafter in a freely detachable manner.

In addition, the apparatus main body 1 is provided with various probes which are connected to dispensing units not shown in the figure. At first, a probe 10 for samples is provided in the vicinity of the above-mentioned sampler 2, a first reagent probe 11 for the first reagent is provided in the vicinity of the first reagent tray 7a, and a second reagent probe 12 for the second reagent is provided in the vicinity of the second reagent tray 7b. The first reagent probe 11 sucks a given amount of a reagent contained in a given reagent container 8 set on the first reagent tray 7a. Then, the first reagent probe 11 is moved above a cuvette 6 on the reaction disk 5 by performing the upward movement and rotational movement shown by arrows (FIG. 2), and the reagent sucked into the probe is dispensed into the cuvette 6. The sample probe 10 sucks a predetermined amount of a sample contained in a sample cup 3 which has been indexed at the predetermined sample sucking position, and the thus sucked sample is delivered into a cuvette 6 on the reaction disk 5 by performing the up and down movement as well as the rotational movement. Further, the second reagent probe 12 sucks a reagent contained in a reagent container 8 on the second reagent tray 7b indexed at a predetermined position and delivers the thus sucked reagent into a cuvette 6 on the reaction disk 5.

On the apparatus main body 1 there are further provided a keyboard 13 and a CRT 14. By operating the keyboard 13, it is possible to enter into a CPU not shown analytic conditions such as dispensing amounts of samples, dispensing amounts of reagents, measuring wavelengths, concentration calculation coefficients and the like depending on respective analytic items. The operator can confirm the entered data by monitoring the display on the CRT 14.

There is further provided a controller (not shown in the drawing) for controlling the analyzing operation on the basis of the entered analytic conditions for respective analytic items as well as identification signals obtained by reading identification labels affixed on to the reagent containers 8 and identification codes provided on the reagent trays 7a and 7b.

In the automatic analyzer of the present invention, samples and reagents are dispensed into the cuvettes 6 on the reaction disk 5 to prepare test liquids, and the test liquids are measured with predetermined wavelengths corresponding to the analytic items at a measuring position after elapsing a predetermined reaction time. Then, analyzed data is obtained by using measured values thereof and concentration calculation coefficients depending on analytic items, and the analyzed data is printed on test result reports by a printer not shown in the figure.

Figure 2:
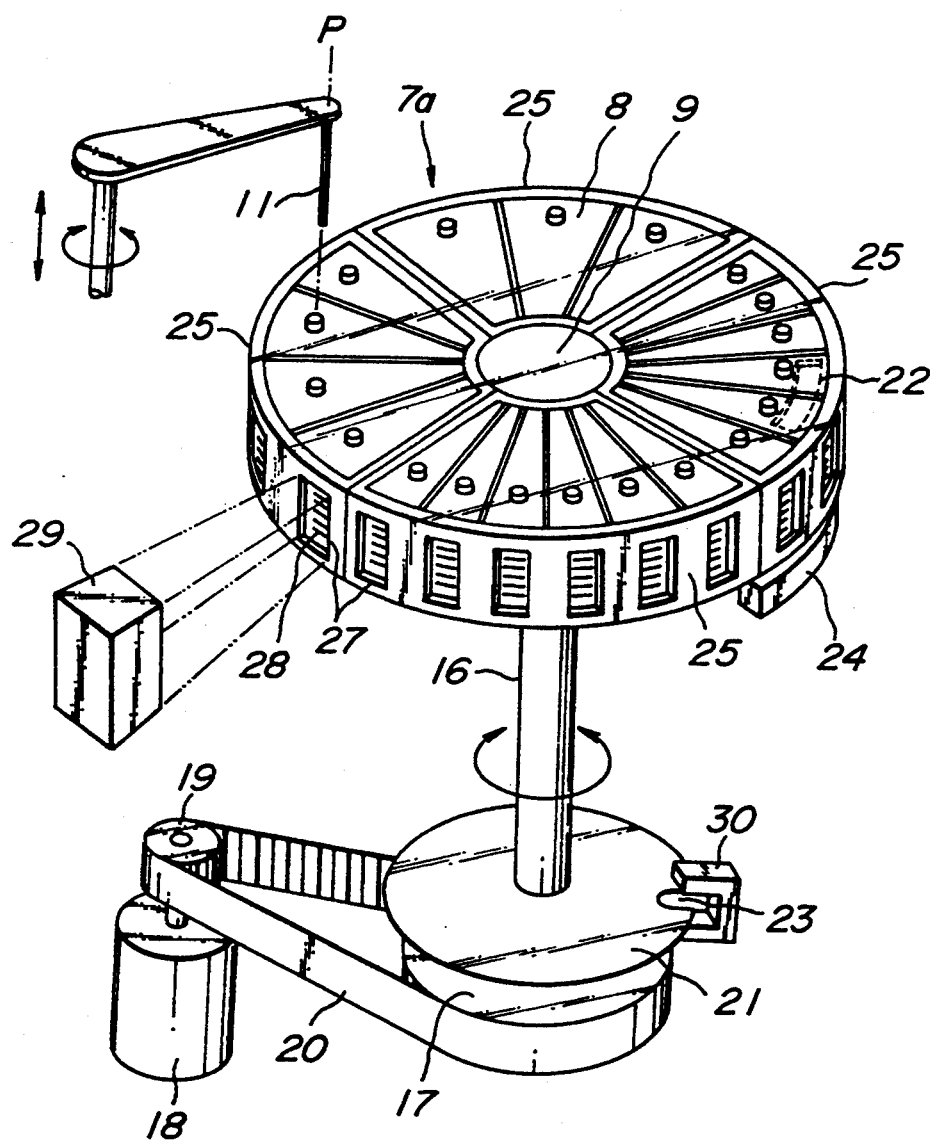
FIG. 2 is a perspective view showing the reagent tray.
Figure 3:
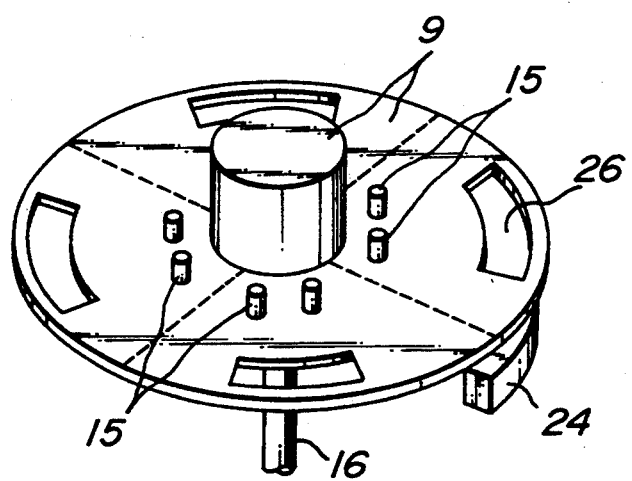
FIG. 3 is a perspective view depicting the turn table.

FIG. 2 and FIG. 3 are perspective views showing the detailed construction of the first reagent tray 7a. It should be noted the second reagent tray 7b has the same construction as that of the first reagent tray 7a. As shown in FIG. 2, a plurality of divided trays 25 are placed on a turn table 9 whose detailed construction is depicted in FIG. 3. Guide pins 15 are provided on the turn table 9, and the divided trays 25 are arranged on the turn table by means of the guide pins 15. In the present embodiment, the divided tray 25 has a sector shape having a center angle of 90 degrees, so that four divided trays are arranged on the turn table 9 circularly.

The turn table 9 is provided with a driving shaft 16 at the central position as shown in FIG. 2, and a pulley 17 is fixed to the end portion of the driving shaft 16. A pulse motor 18 is arranged in the vicinity of the pulley 17, and a timing belt 20 is provided with tension between a driving pulley 19 connected to the pulse motor 18 and the above-mentioned pulley 17. The driving force of the pulse motor 18 is transmitted to the pulley 17 through the driving pulley 19 and the timing belt 20 so as to provide rotational movement of the turn table 9.

The driving shaft 16 is connected with a detection plate 21, and a slit 23 is formed at a predetermined position on the circular circumference of this detection plate 21. Identification codes 22 such as bar codes are affixed to bottom portions of the divided trays 25. It should be noted that the slit 23 is provided at an origin of the turn table 9 and is detected by a first optical detector 30 comprising a light source and a light receiving element. According to the invention, it is also possible to form a plurality of slits 23 in the detection plate 21 and the corresponding number of first optical detectors 30 arranged equidistantly along the periphery of the detection disk and output signals from these detectors may be counted by a suitable counter. Further, the turn table 9 is provided with a second detector 24 such as a bar code reader for detecting optically the identification code 22 provided on the above-mentioned divided tray 25. Incidentally, as shown in FIG. 3, windows 26 for the identification codes are formed in the turn table 9 at positions corresponding to the divided trays, and the identification codes 22 of the divided trays can be optically read through the windows 26.

Figure 4:
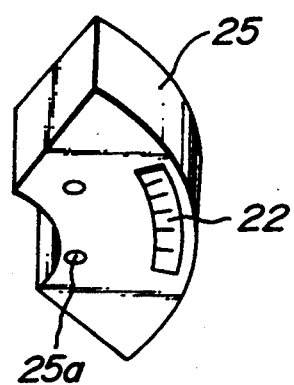
FIG. 4 is a perspective view showing the divided tray.

FIG. 4 is a perspective view of the divided tray 25 as viewed from the bottom face, in which 22 is the identification code, and 25a is a hole for fitting to a guide pin 15 provided on the turn table 9. The reagent tray 7a has formed therein a plurality of compartments for installing a plurality of reagent containers 8. For instance, when there are prepared the reagent containers 8 having capacities of 20 ml, 40 ml, 80 ml, 160 ml and 320 ml, the compartments of the divided trays 25 are constructed to receive these reagent containers. The information for denoting such a plurality of compartments is contained in the above-mentioned identification code 22 provided on the individual divided tray 25. This identification code 22 indicates the information about the size and the number of compartments formed therein. In addition, as shown in FIG. 2, the divided trays 25 are provided with windows 27 for reading reagent identification labels 28 such as bar codes applied on the reagent containers 8 and the information of the reagent contained in the containers 8 is read out optically by a third optical detector 29 such as a bar code reader secured to the apparatus main body 1 shown in FIG. 1 at any position along the reagent tray 7a and provided in the vicinity of the reagent tray. An identification label 28 applied on a reagent container 8 bears information about a reagent contained therein. It should be noted that the third detector 29 may detect whether or not a reagent container is actually set on the divided tray 25.

Figure 6A:
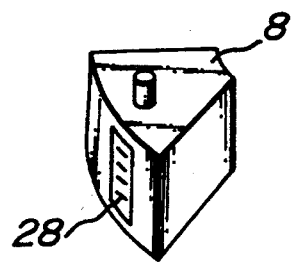
FIGS. 6A and 6B are perspective views depicting another set of the divided tray and reagent container.
Figure 6B:
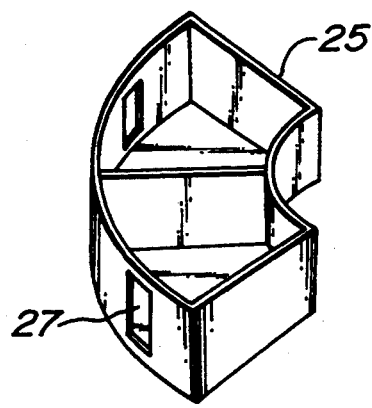

FIG. 5 and FIG. 6 are perspective views showing relations between the divided trays 25 and the reagent containers 8. A divided tray 25 shown in FIG. 5 comprises four small compartments for installing therein four small reagent containers 8 which contain reagents whose dispensing amounts are small. A divided tray 25 illustrated in FIG. 6B comprises two large compartments for accommodating large reagent containers 8 whose dispensing amounts are large. For instance, the reagent container 8 shown in FIG. 5A contains a condensed reagent and the reagent container 8 depicted in FIG. 6A contains a general reagent which is used without being diluted.

In the divided tray 25 shown in FIG. 5B, the four small reagent containers 8 are detachably set in the compartments of the divided tray 25, and in the divided tray 25 illustrated in FIG. 6B, the two large reagent containers 8 are detachably set in the compartments of the divided tray 25. These divided trays 25 are placed on the turn table 9 as shown in FIG. 2. In this manner, according to the invention the reagent containers 8 having different sizes can be set on the turn table 9 in accordance with the kinds of reagents and dispensing amounts. That is to say, a desired combination of the condensed reagents whose dispensing amounts are small and the general reagents whose dispensing amounts are large may be set on the turn table 9.

Next, the operation of the present analyzer will be explained. Since the reagent trays are constituted as described above, when a start button not shown in the figure is depressed, the turn table 9 is rotated by the pulse motor 18 as shown in FIG. 2, and the slit 23 of the detection plate 21 is detected by the first detector 30, thereby the slit 23 is stopped at the origin. As explained above, the second reagent tray 7b is constructed in the entirely the same manner as that of the first reagent tray 7a, and the turn table of the second reagent tray 7b is also indexed into the origin.

At the origin, the identification codes 22 provided on the bottoms of the first divided trays 25 of the reagent trays 7a and 7b are read out by the second detectors 24, and the thus read out information about the first divided trays 25 is stored in the CPU. Next, after the reagent trays 7a and 7b have been rotated by 90 degrees, the identification codes 22 of the second divided trays 25 are read out and the thus read out division information thereof is stored in the CPU. This operation is successively performed to return to the first divided trays, the slit 23 is detected by the detector 30 again and the turn tables 9 are stopped at the origin. In this manner, the division information about all the eight divided trays 25 of the first and second reagent trays 7a and 7b is read out of these divided trays and is stored in the CPU. Then, the CPU can produce commands for driving the reagent trays 7a and 7b such that desired reagents contained in the reagent containers 8 are indexed into reagent suction positions P by rotating the turn tables 9 in clockwise or counterclockwise direction.

Before initiating the actual analysis, on the basis of the above-mentioned division information of the reagent trays 7a and 7b, the reagent containers 8 are stopped one by one in front of the third detectors 29 (FIG. 2), and the reagent identification label 28 is read out by the third detector 29 and is stored in the CPU. In accordance with the reagent identifying information stored in the CPU, the analyzing operation can be controlled depending on analytic conditions inputted beforehand from the keyboard 13.

When the analyzing operation is started, the turn table 9 is rotated in clockwise or counterclockwise direction by the pulse motor 18 on the basis of the division information read by the second detector 24, reagent information read out by the third detector 29 and the analytic conditions entered from the keyboard 13 so as to transport a reagent container 8 containing a reagent which is destined to be used for analyzing a required test item into the reagent suction position P, while the origin of the turn tables 9 is detected by the first detectors 30. Thus dispensing is performed into the cuvette 6 on the reaction disk 5, and after dispensing other reagents and dispensing samples, necessary automatic analysis is performed.

Figure 8:
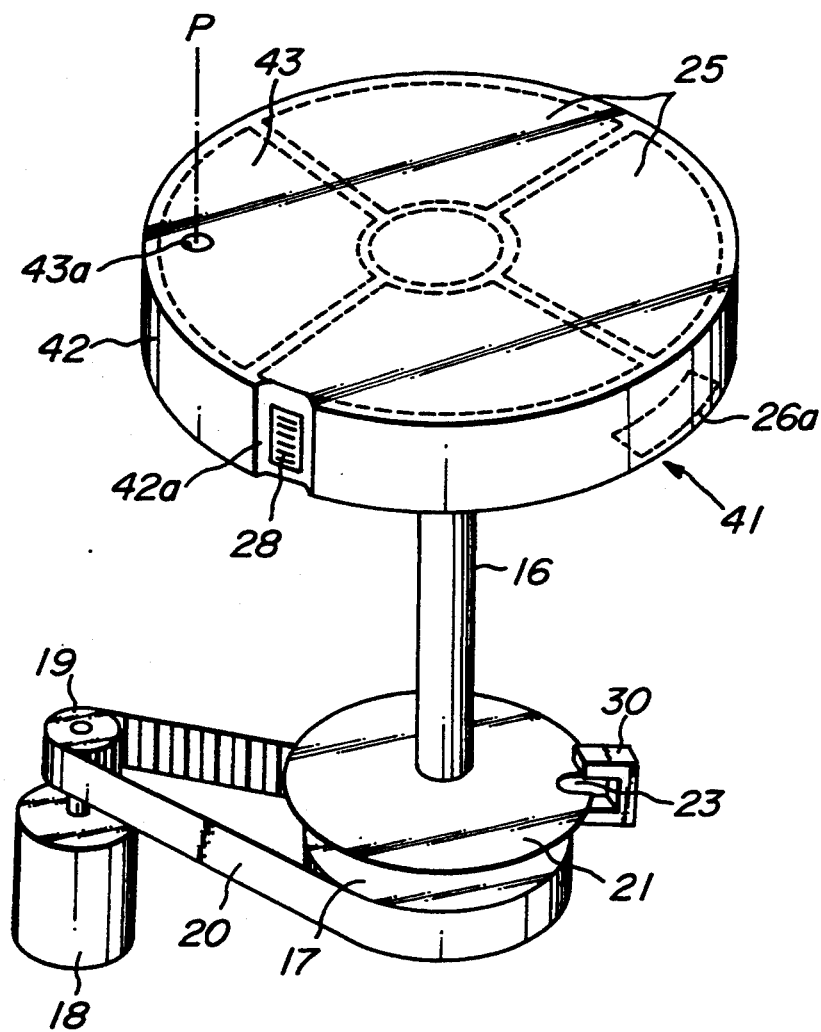
FIG. 8 is a perspective view illustrating the reagent tray installed in the cooling box.

FIG. 8 is a perspective view showing the reagent tray according to the invention, which is installed in a cooling box. In order to avoid evaporation and alternation of the reagents contained in the reagent containers, it is preferable to keep the reagent at a low temperature. To this end, in the present embodiment, the reagent tray 7a is rotatably installed in a cooling box 41 including a main body 42 for effecting the heat insulating with respect to the reagent containers and a lid 43 which is detachably secured to the main body 41 in an airtight manner. In the lid 43, there is formed a small hole 43a at position corresponding to the reagent sucking position P and the probe of the reagent delivery unit is inserted into the reagent container through the hole 43a. In a side wall of the main body 42 there is formed window 26a and 42a through which the reagent identification labels 28 applied on the reagent containers can be read out. These windows 26a and 42a are made of transparent material such as acrylic resin and are provided at positions corresponding to the second and third detectors 24 and 29, respectively as shown in FIG. 2. The shaft 16 secured to the turn table 9 is projected from the bottom wall of the main body 42, while the cooling box 41 is secured to the apparatus main body 1 shown in FIG. 1 such that the cooling box is not rotated with the turn table 9 to minimize the number of the holes 43a and windows 26a, 42a, but the reagent tray 7a can rotate with the turn table 9 to perform the selective dispensing operation described above.

It should be noted that the lid 43 of the cooling box 41 may be advantageously made of transparent material so that the divided trays 25 may be seen through the lid. Further, there is provided a device for supplying a cooling medium into the cooling box 41, although such a device is not shown in FIG. 8. In this embodiment, the second and third optical detectors 24 and 29 may be secured on the main body 42 of the cooling box 41 at positions corresponding to said windows 26a and 42a, respectively.

Figure 7:
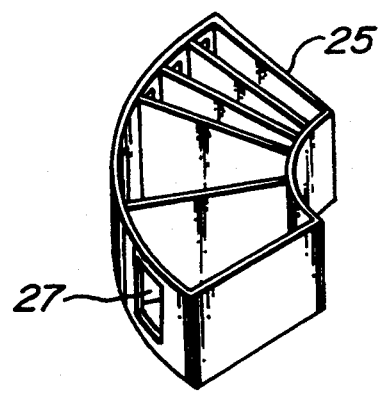
FIG. 7 is a perspective view showing another embodiment of the divided tray according to the invention.

The present invention is not limited to the above-mentioned example, for which various changes and modifications are possible. For instance, the third optical detector 29 may be provided at the same position as the second detector 23 to get both information of the identification labels 28 from the side direction and the identification code 22 from the below simultaneously. Further, the divided tray may be formed as shown in FIG. 7 in which large and small reagent containers can be placed in a mixed manner. Alternatively, although the four divided trays are placed on the turn table, it is also to arrange different number of divided trays other then four and to rotate the turn table at different angles in accordance with the number of the divided trays. For instance, six or eight divided trays may be placed on the turn table. Alternatively, it is also available to give the constitution that the division information having been held by the divided tray may be held by the reagent container together with the reagent information. For instance, windows may be formed in the bottoms of the divided trays 25 as well as in the turn table 9 such that the bottoms of all the reagent containers 8 may be seen, and the identification labels 28 may be provided on the bottoms of the reagent containers 8 and the identification codes 22 may be provided on the side walls of the divided trays 25. In this case, the second and third detectors 24 and 29 have to be exchanged from each other. The divided trays 25 and turn table 9 may be made of transparent material, and then the above-mentioned windows may be dispensed with.

Moreover, the identification code 22 provided on the bottom of the divided tray 25 may be of a rewritable type such as magnetic tape and opto-magnetic record medium and the second detector 24 may be formed by a magnetic head. Then, the information about the set positions of the reagent containers 8 in the divided tray 25 and the contents of the reagents may be written on such a record medium, so that the window 27 and third detector 29 may be dispensed with and the construction of the analyzer becomes simple. Further, in case of providing the window 27, a level of a reagent contained in a reagent container 8 may be detected by means of electrostatic type level meter or light transmission type level meter through the window 27.

Further, both the division identification code and reagent identification code may be applied on a side wall of a divided tray, so that both the division identification information and reagent identification signals may be derived by a single detector. In this case, when these division and reagent identification codes may be formed as a bar code, the reagents set on the divided tray could not be changed at will. However, when these identification codes are recorded on a rewritable type record medium, the reagent identification code can be rewritten so that any reagents may be set on the divided tray.

As described above, according to the present invention, necessary reagents can be prepared beforehand only in necessary amounts, and it becomes unnecessary for the user to frequently exchange reagent containers. In addition, necessary reagents are set in the divided tray in a collected manner, so that it is possible to handle the whole with the divided tray without individually handling reagent containers, so that the handling of reagent containers becomes easy. In addition, reagents may be set for every divided tray in accordance with a combination of items, thereby the combination of analytic items can be easily changed only by exchanging divided trays.

What is claimed is:

1. An automatic analyzer comprising:
a sample holding means for holding a number of samples to be analyzed and indexing successive samples into a sample sucking position;
a sample dispensing means for dispensing samples indexed into said sample sucking position into reaction vessels;
a reagent holding means for holding a plurality of different kinds of reagents and indexing any desired reagents into a reagent sucking position, said reagent holding means including a turn table, a driving means for rotating said turn table, a plurality of divided trays having compartments detachably arranged on said turn table, said compartments for a tray being different in number from at least one other tray, the compartments for each tray being the same or different in size, a reagent container detachably installed in each compartment, a first detector for detecting a position of said turn table to derive a position signal, and a second detector for detecting division identification marks provided on said divided trays to provide a division information signal, said division identification marks provide an indication of size and number of compartments formed in said divided trays;
a reagent dispensing means for dispensing reagents indexed at said reagent sucking position into the reaction vessels;
a measuring means for measuring test liquids contained in the reaction vessels after elapsing given reaction time; and
a controlling means for controlling said driving means in the reagent holding means and reagent dispensing means in accordance with said position signal generated by said first detector as well as said division information signal generated by said second detectors, respectively.

2. An analyzer according to claim 1, wherein said division identification mark is formed by a rewritable type record medium on which a reagent identification signal is recorded, and said controlling means controls said driving means and reagent dispensing means in accordance with said reagent identification signal read out of said division identification mark in addition to said position signal and division information signal.

3. An analyzer according to claim 1, wherein said controlling means comprises a third detector for detecting reagent identification marks provided on the respective reagent containers to produce a reagent identification signal, and said controlling means controls said driving means and reagents dispensing means in accordance with a reagent identification signal read out of said reagent identification mark in addition to said position signal and division information signal.

4. An analyzer according to claim 1, wherein said compartments of the divided tray of the reagent holding means have the same size such that a plurality of reagent containers having the same size may be installed in these compartments.

5. An analyzer according to claim 1, wherein said compartments of the divided tray of the reagent holding means have different sizes such that a plurality of reagent containers having different sizes may be installed in these compartments.

6. An analyzer according to claim 1, wherein said divided trays are formed as sectors having the same center angle and a plurality of divided trays are arranged equidistantly on said turn table circularly.

7. An analyzer according to claim 6, wherein said divided trays are formed as sectors having the center angle of 90 degrees and four divided trays are set on the turn table.

8. An analyzer according to claim 1, wherein said division identification marks are provided on outer bottom surfaces of said divided trays and said turn table has formed therein a plurality of windows through which said second detector can detect said division identification marks.

9. An analyzer according to claim 3, wherein said reagent identification marks are provided on side walls of said reagent containers and said divided trays have formed therein windows through which said reagent identification marks can be detected through said windows.

10. An analyzer according to claim 1, wherein said divided trays are secured onto said turn table by the engagement of pins provided on the turn table and holes formed in bottoms of the divided trays.

11. An analyzer according to claim 1, wherein said reagent holding means further comprises a disk which is rotated with said turn table has formed therein a cut-out portion and said first detector detects said cut-out portion of the disk to derive an origin signal as said position signal.

12. An analyzer according to claim 6, wherein said turn table and divided trays set on the turn table are installed in a cooling box having formed therein a window through which said division identification marks are detected and a reagent sucking hole through which reagents contained in the reagent containers are sucked.

13. An analyzer according to claim 1, wherein said division identification marks are applied on said trays together with reagent identification marks such that said division identification marks and reagent identification marks are detected by said second detector to derive division information signal and reagent information signal.

14. An analyzer according to claim 13, wherein said reagent identification mark is recorded on a rewritable type record medium.

15. An analyzer according to claim 13, wherein said division identification marks and reagent identification marks are provided on side walls of said divided trays.

16. An analyzer according to claim 13, wherein said division identification marks and reagent identification marks are provided on bottom walls of said divided trays.

17. An analyzer according to claim 8, wherein said turn table and divided trays set on the turn table are installed in a cooling box having formed therein a window through which said division identification marks are detected and a reagent sucking hole through which reagents contained in the reagent containers are sucked.

18. An analyzer according to claim 9, wherein said turn table and divided trays set on the turn table are installed in a cooling box having formed therein a window through which said division identification marks are detected and a reagent sucking hole through which reagents contained in the reagent containers are sucked.

* * * * *